United States Patent
Walton et al.

(10) Patent No.: US 11,657,497 B2
(45) Date of Patent: May 23, 2023

(54) METHOD AND APPARATUS FOR REGISTRATION OF DIFFERENT MAMMOGRAPHY IMAGE VIEWS

(71) Applicant: The Johns Hopkins University, Baltimore, MD (US)

(72) Inventors: William C. Walton, Severn, MD (US); Seung-Jun Kim, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 402 days.

(21) Appl. No.: 16/829,556

(22) Filed: Mar. 25, 2020

(65) Prior Publication Data

US 2020/0311923 A1 Oct. 1, 2020

Related U.S. Application Data

(60) Provisional application No. 62/823,972, filed on Mar. 26, 2019.

(51) Int. Cl.
*G06T 7/00* (2017.01)
*G06T 3/00* (2006.01)
*A61B 6/00* (2006.01)

(52) U.S. Cl.
CPC ............ *G06T 7/0012* (2013.01); *A61B 6/502* (2013.01); *A61B 6/5217* (2013.01); *G06T 3/0093* (2013.01); *G06T 2207/20081* (2013.01); *G06T 2207/20084* (2013.01); *G06T 2207/30068* (2013.01); *G06T 2207/30096* (2013.01)

(58) Field of Classification Search
CPC .............. G06T 7/0012; G06T 3/0093; G06T 2207/20081; G06T 2207/20084; G06T 2207/30068; G06T 2207/30096; G06T 7/30; G06T 3/0081; A61B 6/502; A61B 6/5217
USPC ........................................................ 600/408
See application file for complete search history.

(56) References Cited

U.S. PATENT DOCUMENTS

| | | | | |
|---|---|---|---|---|
| 2011/0305313 A1* | 12/2011 | Sklansky | ............... | A61B 6/502 378/37 |
| 2015/0235364 A1* | 8/2015 | Aguirre-Valencia | ....... | G06T 7/0014 382/131 |
| 2019/0057778 A1* | 2/2019 | Porter | .................... | G16H 50/50 |
| 2020/0111211 A1* | 4/2020 | Zeng | ..................... | G06V 10/46 |

(Continued)

OTHER PUBLICATIONS

J. Long et al., "Fully Convolutional Networks for Semantic Segmentation," 2015 IEEE Conference on Computer Vision and Pattern Recognition (CVPR), Boston, MA, 2015, pp. 3431-3440.

(Continued)

*Primary Examiner* — Van D Huynh
(74) *Attorney, Agent, or Firm* — Todd R. Farnsworth

(57) ABSTRACT

A method of identifying potential lesions in mammographic images may include operations executed by an image processing device including receiving first image data of a first type, receiving second image data of a second type, registering the first image data and the second image data by employing a CNN using pixel level registration or object level registration, determining whether a candidate detection of a lesion exists in both the first image data and the second image data based on the registering of the first image data and the second image data, and generating display output identifying the lesion.

20 Claims, 12 Drawing Sheets

(56) References Cited

U.S. PATENT DOCUMENTS

2021/0204897 A1* 7/2021 Fukuda .................. G06T 11/008
2021/0228170 A1* 7/2021 Fukuda .................. A61B 6/545
2022/0036544 A1* 2/2022 Sunwoo .................... G06T 1/20

OTHER PUBLICATIONS

H. Li and Y. Fan, "Non-rigid image registration using fully convolutional networks with deep self-supervision," the Department of Radiology, Perelman School of Medicine, University of Pennsylvania, Sep. 4, 2017.
R. Girshick et al., "Rich Feature Hierarchies for Accurate Object Detection and Semantic Segmentation," from CVPR 14 Proceedings of the 2014 IEEE Conference on Computer Vision and Pattern Recognition at pp. 580-587, 2014.
L. C. Miller, "Mammography Positioning: Basic and Advanced," 2016.
D. Porter et al., "Multimodality Machine Learning for Breast Cancer Detection: Synergistic Performance with Upstream Data Fusion of Digital Breast Tomosynthesis and Ultrasound," Machine Learning for Health Care, Stanford, CA, Aug. 2018.
Y. Guo et al., "Breast image registration techniques: a survey," Med Biol Eng Comput (2006) 44: 15-26.
J. Hipwell et al., "A New Validation Method for X-ray Mammogram Registration Algorithms Using a Projection Model of Breast X-ray Compression," IEEE Transactions on Medical Imaging, vol. 26, No. 9, Sep. 2007.
G. Litjens et al., "A survey on deep learning in medical image analysis," Medical Image Analysis 42 (2017) 60-88.
J. Lee et al., "Deep Learning in Medical Imaging: General Overview," Korean J Radiol 2017;18(4):570-584, 2017.
F. Alam et al., "Intrinsic registration techniques for medical images: A state-of-the-art review," J Postgrad Med Inst 2016; 30(2): 119-32, 2016.
P. M. Francisco et al., "Medical image registration: a review," Computer Methods in Biomechanics and Biomedical Engineering, 17:2, 73-93, 2014.
R. Shams et al., "A Survey of Medical Image Registration on Multicore and the GPU," IEEE Signal Processing Magazine, vol. 27, No. 2, 2010.
L. G. Brown, "A Survey of Image Registration Techniques," ACM Computing Surveys, vol. 24, No. 4, 1992.
C. Wachinger, "MICCAI 2010 Tutorial: Intensity-based Deformable Registration—Similarity Measures," 2010.
N. Ruiter et al., "Elastic registration of x-ray mammograms and three-dimensional magnetic resonance imaging data," Journal of Digital Imaging, vol. 14, No. 2, pp. 52-55, 2001.
T. Hopp et al., "Automatic multimodal 2D/3D breast image registration using biomechanical FEM models and intensity-based optimization," Medical Image Analysis, vol. 17, pp. 209-218, 2013.
M. Samulski et al., "Matching mammographic regions in mediolateral oblique and cranio caudal views: a probabilistic approach," Proc. of SPIE vol. 6915, 69151M, (2008).
Y. Kita et al., "Correspondence between Different View Breast X Rays Using Curved Epipolar Lines," Computer Vision and Image Understanding 83, 38-56 (2001).
Y. Kita et al., "Correspondence between different view breast X-rays using a simulation of breast deformation," in Proceedings. 1998 IEEE Computer Society Conference on Computer Vision and Pattern Recognition, Santa Barbara, CA, USA, 1998.
J. Krebs et al., "Robust Non-rigid Registration Through Agent-Based Action Learning," International Conference on Medical Image Computing and Computer-Assisted Intervention, Quebec City, Canada, 2017.
B. D. d. Vos et al., "End-to-End Unsupervised Deformable Image Registration with a Convolutional Neural Network," International Workshop on Deep Learning in Medical Image Analysis, Quebec City, Canada, 2017.
H. Sokooti et al., "Nonrigid Image Registration Using Multi-scale 3D Convolutional Neural Networks," International Conference on Medical Image Computing and Computer-Assisted Intervention, Quebec City, Canada, 2017.
I. Yoo et al., "ssEMnet: Serial-Section Electron Microscopy Image Registration Using a Spatial Transformer Network with Learned Features," International Workshop on Deep Learning in Medical Image Analysis, Quebec City, Canada, 2017.
K. Eppenhof et al., "Deformable image registration using convolutional neural networks," Proc. SPIE 10574, Medical Imaging 2018: Image Processing, 105740S (Mar. 2, 2018).
X. Yang et al., "Quicksilver: Fast predictive image registration—A deep learning approach," NeuroImage 158 (2017) 378-396.
S. Miao et al., "A CNN Regression Approach for Real-Time 2D/3D Registration," IEEE Transactions on Medical Imaging, vol. 35, No. 5, May 2016.
S. Perek et al., "Mammography Dual View Mass Correspondence," Computer Vision and Pattern Recognition, 2018.
D. Zikic, "MICCAI 2010 Tutorial: Intensity-based Deformable Registration—Overview of Intensity-based Deformable Registration," 2010.
M. Staring, "MICCAI 2010 Tutorial: Intensity-based Deformable Registration—Regularization in Deformable Registration," 2010.
V. Vishnevskiy et al., "Total Variation Regularization of Displacements in Parametric Image Registration," International MICCAI Workshop on Computational and Clinical Challenges in Abdominal Imaging, Cambridge, MA, 2014.
H. Su et al., "Multi-View Convolutional Neural Networks for 3D Shape Recognition," IEEE International Conference on Computer Vision, Santiago, Chile, 2015.
Q. Fang et al., "Tetrahedral mesh generation from volumetric binary and gray-scale images," in Proceedings of IEEE International Symposium on Biomedical Imaging, 2009.
R. S. Lee et al., "A curated mammography data set for use in computer-aided detection and diagnosis research," Scientific Data, vol. 4, 2017.
A. Krizhevsky, "Learning Multiple Layers of Features from Tiny Images," 2009.
E. Garcia et al., "Breast MRI and X-ray mammography registration using gradient values," Medical Image Analysis 54 (2019) 76-87.
T. Mertzanidou et al., "MRI to X-ray mammography intensity-based registration with simultaneous optimisation of pose and biomechanical transformation parameters," Medical Image Analysis 18 (2014) 674-683.
Hu et al., Label-Driven Weakly-Supervised Learning for Multimodal Deformable Image Registration, 2018 IEEE 15th International Symposium on Biomedical Imaging (ISBI 2018) Apr. 4-7, 2018, Washington, D.C., USA.
Balakrishnan et al., VoxelMorph: A Learning Framework for Deformable Medical Image Registration, arXiv, Sep. 1, 2019.

* cited by examiner

METHOD AND APPARATUS FOR REGISTRATION OF DIFFERENT MAMMOGRAPHY IMAGE VIEWS

CROSS-REFERENCE TO RELATED APPLICATIONS

This application claims the benefit of U.S. Provisional Application No. 62/823,972 filed on Mar. 26, 2019, the entire contents of which are hereby incorporated herein by reference.

TECHNICAL FIELD

Example embodiments generally relate to techniques for registration of images and, in particular, relate to an apparatus and method for employing a convolutional neural network (CNN) non-rigid registration algorithm for registration of different mammography images.

BACKGROUND

Breast cancer is one of the leading causes of death for women worldwide with a half million lives lost annually, including 40,000 in the United States alone. Early detection has been shown to be critical for less invasive treatment of breast cancer and for saving lives. Hence, tools and techniques that can aid clinicians in early detection of breast cancer are invaluable. X-ray based two-view mammography is the main imaging modality used for breast cancer screening in asymptomatic women and is also used for more specialized diagnostic exams, which are performed when suspicious findings or symptoms are present. Conventional mammography involves two-dimensional (2-D) Full-Field Digital Mammography (FFDM) or, in recent years, Digital Breast Tomosynthesis (DBT). DBT is a relatively new type of digital mammography which was FDA approved in the United States in 2011.

DBT involves obtaining numerous mammographic images across an arc. Reconstruction generates multiple contiguous 1 mm thick slices through the breast, as well as synthesized 2-D images of the entire breast. DBT images, like FFDM images, are obtained in Craniocaudal (CC) and Mediolateral Oblique (MLO) standard mammographic views. Other modalities such as Ultrasound (US), Magnetic Resonance Imaging (MRI), Positron Emission Mammography (PEM) and Molecular Breast Imaging (MBI) can also be used to image the breast, but X-ray based mammography is the only imaging modality that has been proven to improve outcomes and decrease mortality rates when used as a screening tool.

Mammographic imaging typically involves imaging the breast from at least two different angles. The most frequently used views are the CC and MLO views mentioned above. The name of each view describes the direction of the X-ray beam from the source through the breast to the X-ray detector. Thus, the CC view is obtained at an angle of 0 degrees from the top to the bottom of the compressed breast and the MLO view is obtained at an angle in the range of 45 to 50 degrees from medial near the center of the chest, toward the axilla. Each view involves physically positioning and compressing the breast between two compression plates immediately adjacent to an X-ray source and detector.

The purpose of the two views is to include as much breast tissue as possible, and also to locate lesions by triangulating from these projections. Breast lesions may be visible in both views or only on one view depending on the lesion location in the breast and also depending on the density of the breast tissue. When breast tissue is very dense, meaning it is made up of mostly fibrous and glandular components, it can obscure lesions, as the background breast tissue will have similar x-ray attenuation compared to a lesion, in essence hiding the finding. This is in contrast to mainly fatty breast tissue where lesions have much greater density compared to the fatty tissue, based on the attenuation of the X-ray beam as it travels through breast tissue, making the lesions readily visible.

Currently radiologists analyze images by extrapolating between the two views in search of abnormalities. Seeing a lesion on both views is an important feature, which signals to the radiologist that the lesion is more likely to be real rather than a false alarm. Additionally, in order to better characterize breast lesions, visualizing the finding in two views is beneficial. Finally, identifying a lesion in both views localizes the finding in the breast, which is critical. Thus, precise registration assists clinicians in locating findings, confirming accurate lesion detection, and therefore planning further breast imaging evaluation. Registration is essential to guide biopsies and surgical procedures as accurate information regarding lesion position is required.

Machine learning algorithms and Computer Aided Diagnosis (CAD) processes that involve joint processing (or fusion) of breast images currently exist, and are in development in this area. However, the automated registration of mammographic images has proven to be a challenging task due to the non-rigid heterogeneous nature of breast tissue and due to tissue distortion that can occur as part of breast imaging, including mammographic compression. Moreover, the resulting pixel-wise mappings may not be bijective, but rather involve one-to-many pixel mappings for each pixel. While advancements in deep learning have generally resulted in numerous improvements in medical image processing, recent surveys indicate that a best approach has not yet been identified for medical image registration and that challenges remain in achieving the desired levels of accuracy. Thus, it may be desirable to define an improved automated registration method for mammographic images.

BRIEF SUMMARY OF SOME EXAMPLES

Some example embodiments may enable the provision of a system that is capable of providing an improved registration method and device for execution of the same.

In one example embodiment, a method of identifying potential lesions in mammographic images may include operations executed by an image processing device. The operations may include receiving first image data of a first type, receiving second image data of a second type, registering the first image data and the second image data by employing a CNN using pixel level registration or object level registration, determining whether a candidate detection of a lesion exists in both the first image data and the second image data based on the registering of the first image data and the second image data, and generating display output identifying the lesion.

In another example embodiment, a method of identifying potential lesions in mammographic images via pixel level registration is provided. The method may include operations executed by an image processing device including receiving first image data of a first type, receiving second image data of a second type, learning a mapping from a first image of the first image data to a second image of the second image data by employing a CNN, generating a warped image output based on the mapping, determining whether a candidate detection of a lesion exists in both the first image data and the second image data based on the warped image, and generating display output illustrating the candidate detection.

In still another example embodiment, a method of identifying potential lesions in mammographic images via object level registration is provided. The method may include receiving first image data of a first type, receiving second image data of a second type, identifying candidate regions by employing a first stage CNN architecture configured to independently analyze the first image data and the second image data to identify the candidate regions, conducting pairwise evaluation of the candidate regions to determine whether the candidate detection exists, and determining candidate matches by employing a second stage CNN architecture and generating display output identifying the lesion.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
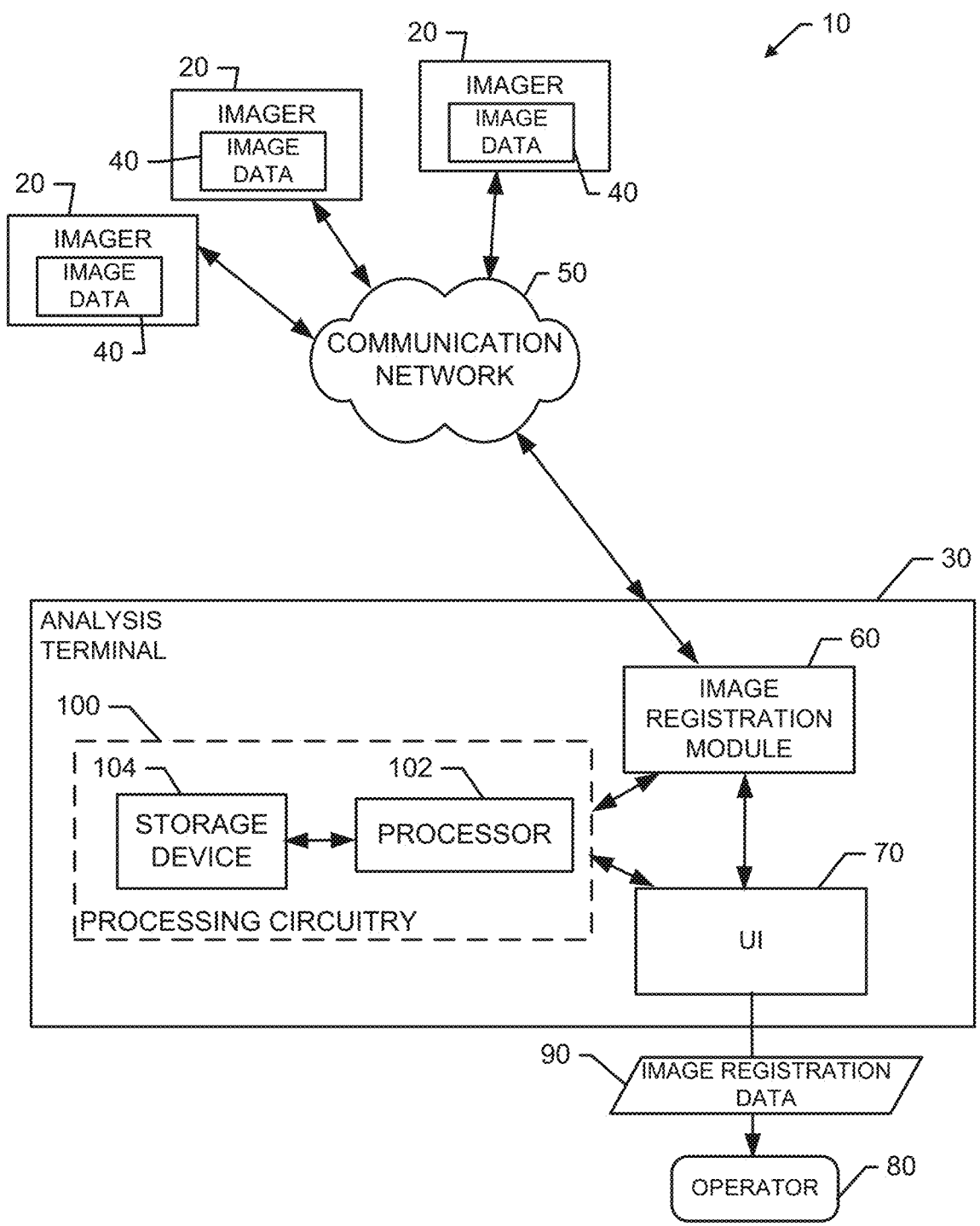
FIG. 1 illustrates a functional block diagram of a system for identifying potential lesions in mammographic images according to an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

As noted above, efforts at image registration between CC and MLO views have, to date, not been able to produce consistently satisfying results. In particular, conventional methods have not been able to use both CC and MLO data sets as a collective set from which the same object (or objects) can be identified in each of the two different views. Example embodiments provide a method and apparatus that provide significantly improved performance in relation to this endeavor, and actually enable detection of the same object in each of the two different views. In this regard, example embodiments provide two different sub-methods for achieving this outcome. One such sub-method employs pixel level registration, while the other employs object level registration. An example embodiment including apparatuses configured to execute the method, and the method (which can employ one of the sub-methods) are described in greater detail below.

In this regard, some example embodiments may relate to the provision of a system that is configured to employ convolutional neural networks (CNNs) to register CC and MLO images in order to find the same object within the images using either pixel level registration or object level registration according to the respective sub-methods described herein. The system may be configured to be integrated with imaging equipment that obtain images of the same tissue from different views (or different collection orientations, including different orientations of the tissue). Thus, for example, the imaging equipment may be configured to process common views from breast x-ray imaging including the CC and MLO images, or supplemental views such as, but not limited to, the ML, LM, LMO. Similarly, the system may be configured to process multiple views from breast ultrasound imagery, such as, but not limited to radial and anti_radial views. Additionally or alternatively, the system may be configured to process multiple views from breast magnetic resonance imaging (MRI), such as, but not limited to, slices between different MRI sequences such as T1 or T2 sequences, or slices from MRI sequences taken at different times. In all cases, such processing may be done either in real time or after the fact for offline processing from the imaging equipment and may then process the images accordingly as described herein. Thereafter, an output may be generated that identifies objects that appear in both images (and therefore may represent potential lesions).

FIG. 1 illustrates a system 10 according to an example embodiment that may include a plurality imaging devices (e.g., imager 20). Notably, although FIG. 1 illustrates three imagers 20, it should be appreciated that many more imagers 20 may be included in some embodiments and thus, the three imagers 20 of FIG. 1 are simply used to illustrate a potential for a multiplicity of imager 20 and the number of imagers 20 is in no way limiting to other example embodiments. Moreover, example embodiments can also be practiced with fewer imagers 20 and including as little as one imager 20.

The example described herein will be related to an asset comprising a programmed computer or analysis terminal (e.g., analysis terminal 30) to illustrate one example embodiment. However, it should be appreciated that example embodiments may also apply to any asset including, for example, any programmable device that is capable of interacting with image data 40 received from portions of a communication network 50 related to image data including CC image data and MLO image data corresponding to an individual patient. Moreover, the processing of the image data 40 as described herein could also be performed for multiple different patients and include data from the same imager 20 or from multiple imagers 20 at the same instance of the analysis terminal 30. Thus, one instance of the analysis terminal 30 may handle image data 40 from multiple imagers and/or patients. However, it should also be appreciated that the communication network 50 of FIG. 1 could be completely eliminated and an instance of the imager 20 could be integrated directly with the analysis terminal 30 in some alternative embodiments.

Each one of the imagers 20 may be understood to be an x-ray machine or other medical imaging machine that is capable of or otherwise configured to generate CC and MLO images that form the image data 40. In some cases, the imagers 20 may also or alternatively be configured to generate other images or views such as medio lateral (ML) and lateral medial (LM) views. Meanwhile, the analysis terminal 30 may include or otherwise be embodied as computing device (e.g., a computer, a network access terminal, laptop, server, a personal digital assistant (PDA), mobile phone, smart phone, tablet, or the like) capable of being configured to perform data processing as described herein. As such, for example, the analysis terminal 30 may include (or otherwise have access to) memory for storing instructions or applications for the performance of various functions and a corresponding processor for executing stored instructions or applications. The analysis terminal 30 may also include software and/or corresponding hardware for enabling the performance of the respective functions of the analysis terminal 30 including, for example, the receipt or processing of the image data 40 and the generation and/or sharing of various content items including the outputs of the analyses performed on the image data 40 by the analysis terminal 30.

The communication network 50 (if employed) may be a data network, such as a local area network (LAN), a metropolitan area network (MAN), a wide area network (WAN) (e.g., the Internet), and/or the like, which may couple one or more instances of the imager 20 to devices such as processing elements (e.g., personal computers, server computers or the like) and/or databases. Communication between the communication network 50, the imager(s) 20 and the devices or databases (e.g., servers) to which the imager(s) 20 are coupled may be accomplished by either wireline or wireless communication mechanisms and corresponding communication protocols. The protocols employed may include security, encryption or other protocols that enable the image data 40 to be securely transmitted without sacrificing patient privacy.

In an example embodiment, the imager 20 may be coupled via the communication network 50 to an image registration module 60. The image registration module 60 may be operably coupled to a user interface 70 to form respective portions of the analysis terminal 30. An operator 80 may be enabled to interface with the analysis terminal 30 via the user interface 70 to operate the image registration module 60 in order to receive object registration data 90 as described in greater detail below.

The analysis terminal 30 of FIG. 1 may represent an apparatus for provision of the image registration capabilities described herein according to an example embodiment. The analysis terminal 30 may be employed, for example, on a device such as, for example, a computer, a network device, server, proxy, or the like at which the image registration module 60 may be instantiated. It should be noted that the devices or elements described below may not be mandatory and thus some may be omitted in certain embodiments.

Referring still to FIG. 1, an apparatus for provision of image registration between CC and MLO images of the image data 40 in accordance with an example embodiment is provided. However, it should be appreciated that the apparatus may also be capable of finding correspondence between either of these views and LM or ML views as well. Thus, the application specifically to CC and MLO views described herein should be appreciated as being a non-limiting example. The apparatus may be an embodiment of the image registration module 60. As such, configuration of the apparatus as described herein may transform the apparatus into the image registration module 60. In an example embodiment, the apparatus may include or otherwise be in communication with processing circuitry 100 that is configured to perform data processing, application execution and other processing and management services according to an example embodiment of the present invention. In one embodiment, the processing circuitry 100, which may include a processor 102 and a storage device 104, may be in communication with or otherwise control the user interface 70 and the image registration module 60. As such, the processing circuitry 100 may be embodied as a circuit chip (e.g., an integrated circuit chip) configured (e.g., with hardware, software or a combination of hardware and software) to perform operations described herein. However, in some embodiments, the processing circuitry 100 may be embodied as a portion of a server, computer, laptop, workstation or even one of various mobile computing devices. In situations where the processing circuitry 100 is embodied as a server or at a remotely located computing device, the user interface 70 may be disposed at another device that may be in communication with the processing circuitry 100 via a network (e.g., communication network 50).

The user interface 70 may be in communication with the processing circuitry 100 to receive an indication of a user input at the user interface 70 and/or to provide an audible, visual, mechanical or other output to the user (e.g., image registration data 90). As such, the user interface 70 may include, for example, a keyboard, a mouse, a joystick, a display, a touch screen, a microphone, a speaker, a cell phone, or other input/output mechanisms. In embodiments where the apparatus is embodied at a server or other network entity, the user interface 70 may be limited or even eliminated in some cases. Alternatively, as indicated above, the user interface 70 may be remotely located. In some cases, the user interface 70 may also include a series of web pages or interface consoles generated to guide the user through various options, commands, flow paths and/or the like for control of or interaction with the image registration module 60. The user interface 70 may also include interface consoles or message generation capabilities to send instructions, warnings, alerts, etc., and/or to provide an output that clearly indicates a correlation between objects in the different types of images (e.g., the CC images and the MLO images) of the image data 40.

In an example embodiment, the storage device 104 may include one or more non-transitory storage or memory devices such as, for example, volatile and/or non-volatile memory that may be either fixed or removable. The storage device 104 may be configured to store information, data, applications, instructions or the like for enabling the apparatus to carry out various functions in accordance with example embodiments of the present invention. For example, the storage device 104 could be configured to buffer input data for processing by the processor 102. Additionally or alternatively, the storage device 104 could be configured to store instructions for execution by the processor 102. As yet another option, the storage device 104 may include one of a plurality of databases that may store a variety of files, contents or data sets, or structures used to embody one or more of the CNNs described herein. Among the contents of the storage device 104, applications may be stored for execution by the processor 102 in order to carry out the functionality associated with each respective application.

The processor 102 may be embodied in a number of different ways. For example, the processor 102 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an example embodiment, the processor 102 may be configured to execute instructions stored in the storage device 104 or otherwise accessible to the processor 102. As such, whether configured by hardware or software methods, or by a combination thereof, the processor 102 may represent an entity (e.g., physically embodied in circuitry) capable of performing operations according to embodiments of the present invention while configured accordingly. Thus, for example, when the processor 102 is embodied as an ASIC, FPGA or the like, the processor 102 may be specifically configured hardware for conducting the operations described herein. Alternatively, as another example, when the processor 102 is embodied as an executor of software instructions, the instructions may specifically configure the processor 102 to perform the operations described herein.

In an example embodiment, the processor 102 (or the processing circuitry 100) may be embodied as, include or otherwise control the image registration module 60, which may be any means such as a device or circuitry operating in accordance with software or otherwise embodied in hardware or a combination of hardware and software (e.g., processor 102 operating under software control, the processor 102 embodied as an ASIC or FPGA specifically configured to perform the operations described herein, or a combination thereof) thereby configuring the device or circuitry to perform the corresponding functions of the image registration module 60 as described herein.

Figure 2:
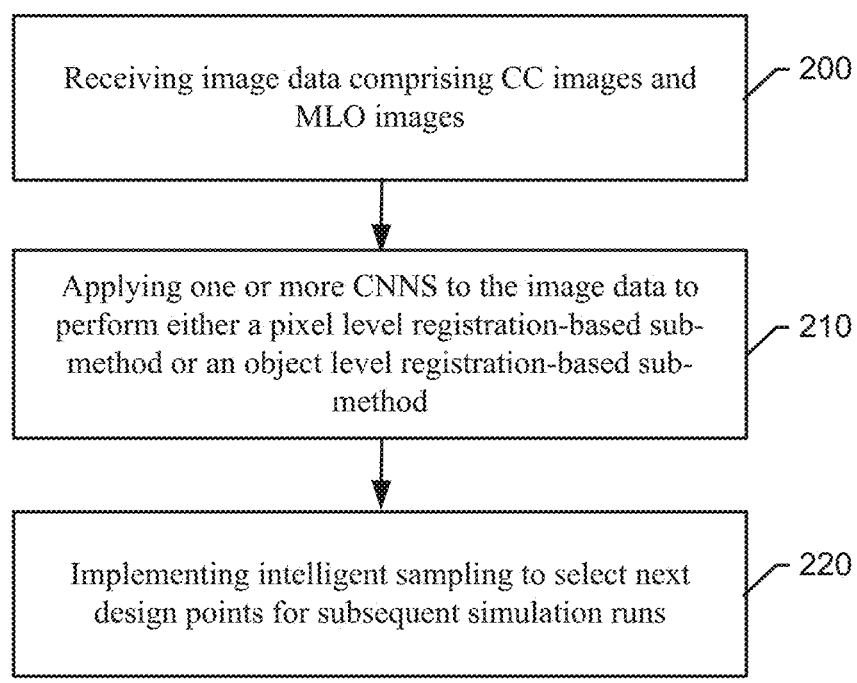
FIG. 2 illustrates a functional block diagram of a method for identifying potential lesions in mammographic images according to an example embodiment.

FIG. 2 illustrates a block diagram showing a high level functioning of the image registration module 60 of an example embodiment. In this regard, the image registration module 60 may be configured to receive the image data 40, which may include CC images and MLO images at operation 200. The image registration module 60 may then be configured to apply the image data 40 to one or more CNNs, where the one or more CNNs are configured to perform either pixel level registration or object level registration-based sub-methods at operation 210. The image registration module 60 may generate object registration data 90 at operation 220 as a result of the application of the one or more CNNs to the image data 40 in operation 210. The object registration data 90 may include an indication of a detection of the same thing (i.e., the same object or anomaly) in the CC images and MLO images of the image data 40.

Of note, the image registration module 60 may be configured to perform only one of the pixel level registration-based sub-method or the object level registration-based sub-method in some cases. However, in other embodiments, the image registration module 60 may be configured to perform both the pixel level registration-based sub-method and the object level registration-based sub-method. In such an example, the operator 80 may use the user interface 70 to select which one of the pixel level registration-based sub-method or the object level registration-based sub-method should be used for a given set of the image data 40. As yet another alternative, the operator 80 may select an option to run both the pixel level registration-based sub-method and the object level registration-based sub-method (an any desired order, or in parallel) to check agreement or potential differences in the object registration data 90 generated by each respective sub-method. The operator may also interface with the object registration data 90 to select regions of interest or potential lesions or to otherwise drive operation of the image registration module 60 in the manner described herein.

Structures and operations associated with each of the pixel level registration-based sub-method and the object level registration-based sub-method will now be described in reference to FIGS. 3-20. In this regard, FIGS. 3-12 will be used to describe pixel level registration and FIGS. 13-20 will be used to describe object level registration in accordance with respective example embodiments. Both sub-methods employ CNNs, which are known by those having skill in the art to include input and output layers with potential for hidden layers or skip paths, and employ convolution (a special kind of linear operation) instead of general matrix multiplication in at least one of the layers. The activation function of a CNN is commonly a rectified linear unit (ReLu) layer, and may be followed by additional convolutions or pooling layers, and a final convolution, among other things. Convolutional layers will convolve the input and pass a result to the next layer. For images, passing through a convolution layer generally abstracts the image to a feature map. Pooling layers tend to reduce the dimensions of data by combining outputs prior to processing at a next layer.

Figure 3A:
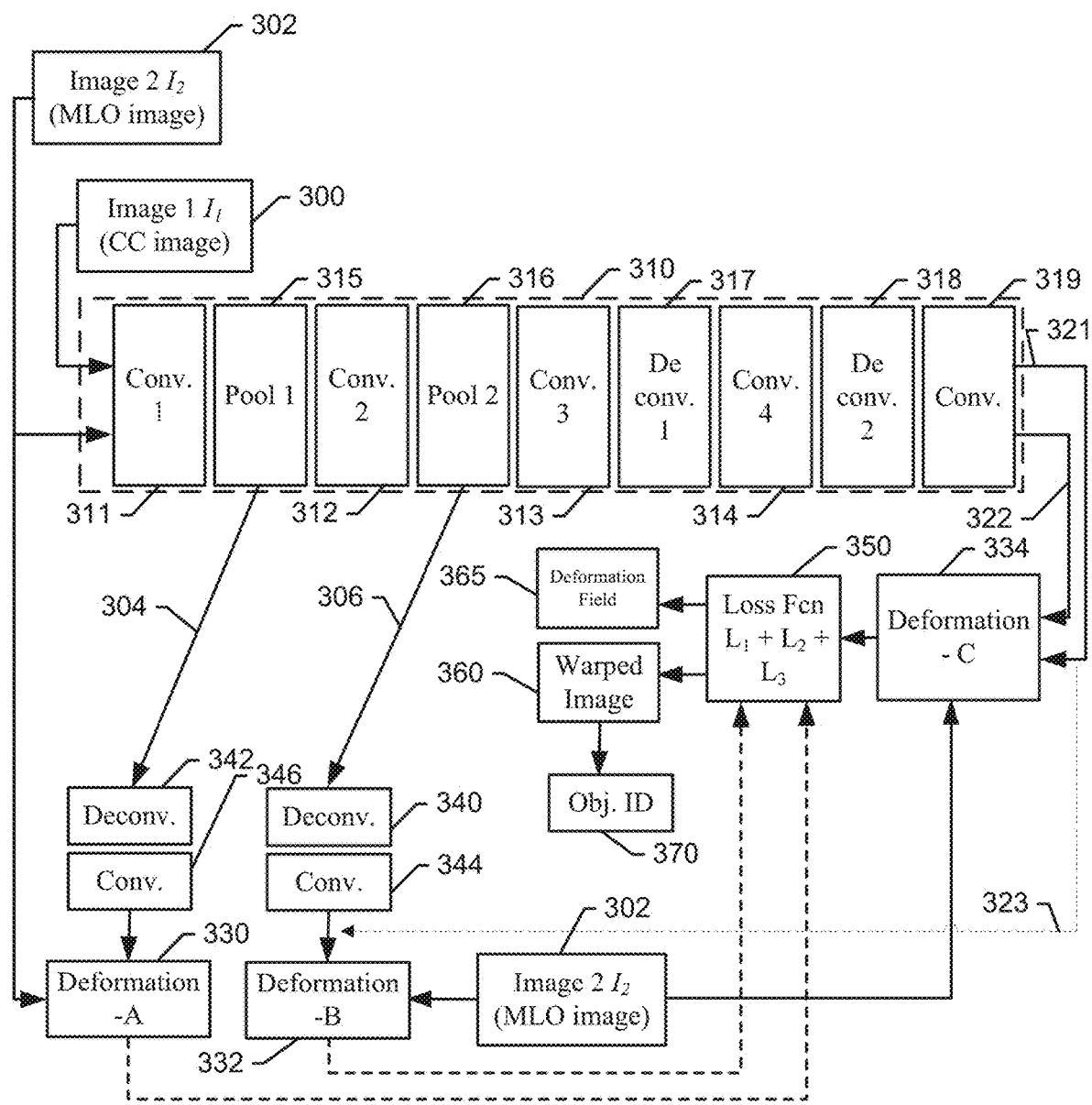
FIG. 3A illustrates an architecture for performing the method of FIG. 2 using pixel level registration in accordance with an example embodiment.

FIG. 3A illustrates an architecture for performing pixel level registration (i.e., executing the pixel level registration-based sub-method) of a first image 300 (i.e., image 1 or $I_1$) and a second image 302 (i.e., image 2 or $I_2$) in accordance with an example embodiment. In particular, the architecture of FIG. 3A employs a deformation-field based CNN network for registering mammographic images. As shown in FIG. 3A, the first image 300 may be a CC image and the second image 302 may be an MLO image. However, either or both of these could be replaced with ML or LM views in various other alternative examples. Various image processing steps will be described in relation to the first and second images 300 and 302 based on the architecture shown in FIG. 3A. However, it should be appreciated that the first and second images 300 and 302 could be swapped with respect to the processing described without changing results thereof. In other words, if the MLO image were instead the first image 300 and the CC image were instead the second image 302 the processing described and results achieved would not change. Moreover, it should also be appreciated that example embodiments may be practiced on multiple instances of each of the first and second images 300 and 302 even though only two specific images are shown in this example.

Figure 3B:
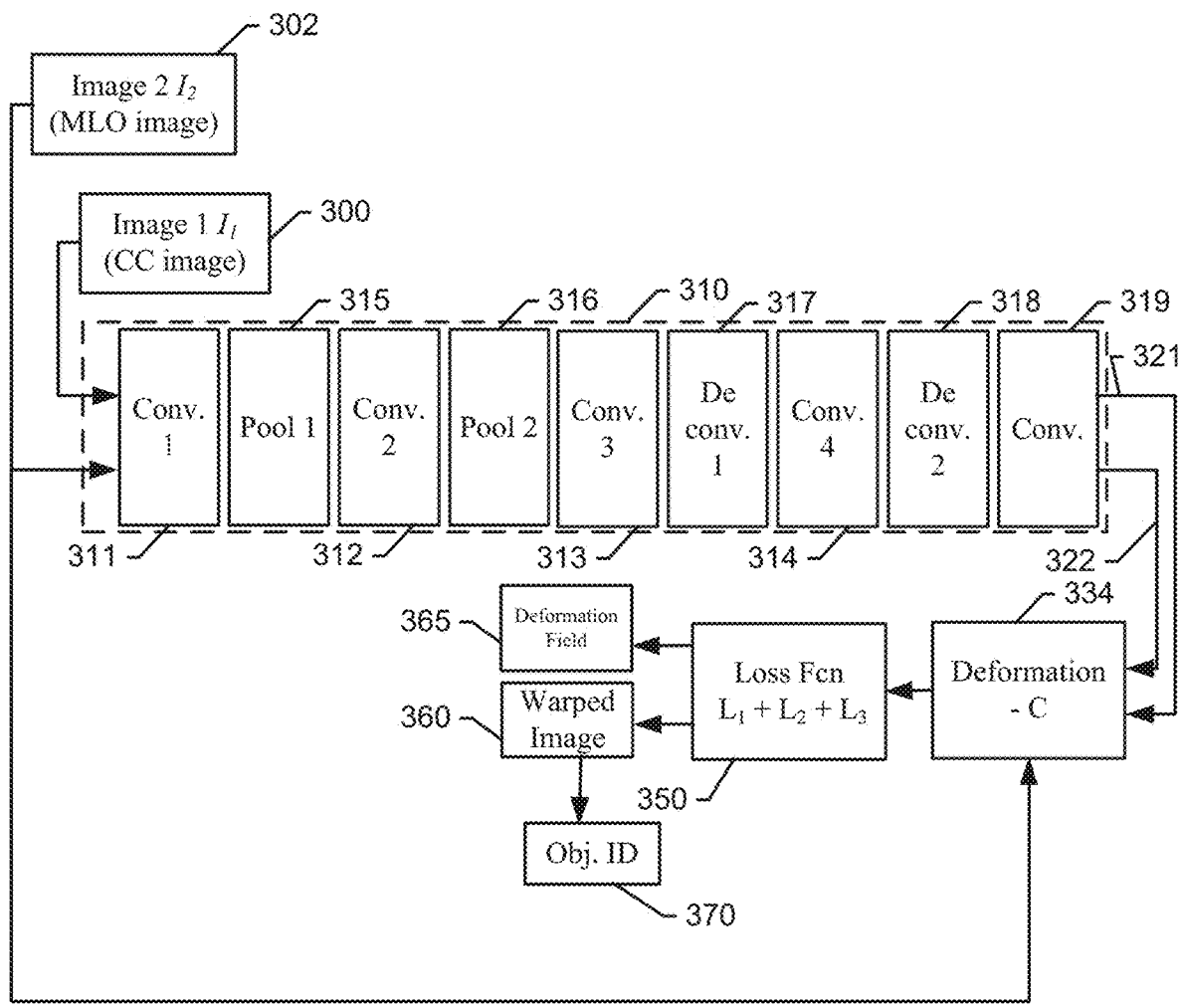
FIG. 3B illustrates an alternative architecture to that of FIG. 3A, which does not include skip paths, in accordance with an example embodiment.

The first and second images 300 and 302 may each be fed into a CNN 310. The input images are pre-processed using custom techniques (some of which are optional). The following are examples. First, as is typical for CNN's, the input images may be resampled to a fixed number of row and column pixels (e.g., 3000×2000). Next, the images may be flipped, if needed, about a vertical axis so that the breast scene is always oriented in a certain direction (e.g., chest-wall or pectoral muscle on the left, and nipple towards the right.) Additionally, image processing may be applied to generate a "mask-image", which is an image raster the same size as the input image, but which only has two gray levels: a foreground gray level representing the breast tissue, and a background value representing the rest of the image. Further, custom image processing algorithms for detecting the location of the breast nipple in each image may be applied. This location information may be used for supporting parts of the loss function 350 during training. Also, exclusive to the MLO input image, custom image processing may be applied for detecting and masking the pectoral muscle in the image. Other, custom image processing may also be applied. It is noted that the minimal required processing above is the input image re-sizing and the image flipping (or the ensuring that the breast scenes are oriented in a certain direction.) The CNN 310 may be a fully convolutional network (FCN) and is not a fully connected CNN, nor does it have fully connected components as some CNN's do. An example of such an FCN is described in J. Long, E. Shelhamer and T. Darrell, "Fully convolutional networks for semantic segmentation," 2015 *IEEE Conference on Computer Vision and Pattern Recognition* (*CVPR*), Boston, Mass., 2015, pp. 3431-3440, the entire contents of which are hereby incorporated herein by reference. Another example of an FCN is described in H. Li and Y. Fan, "Non-rigid image registration using fully convolutional networks with deep self-supervision," the Department of Radiology, Perelman School of Medicine, University of Pennsylvania, Sep. 4, 2017, the entire contents of which are hereby also incorporated herein by reference. A benefit of the FCN not being fully connected is that the CNN's can ingest an input image of arbitrary size and produce an output raster at that same size. On the contrary, with both Fully Connected Networks and even CNNs that use fully connected components in their final layers, the size of the output raster is more so constrained based on the number of output nodes. With an FCN, the same network could be used to process input images of different sizes. (However, in some examples, in the training phase, the network parameters—such as convolution kernel sizes—may be dynamically set based on the size of the input images.) The output products—the warped images and deformation fields—would also have the same size as the inputs. This is not typically true for the other two cases of networks, for which the input and output image sizes tend to be constrained based on the number of input and output nodes (or neurons) and the transfer functions that are used at the output. The CNN 310 may include a skip architecture that includes a first skip path 304 and a second skip path 306 in addition to the main serial path, which extends fully through the CNN 310 from left to right in the image shown in FIGS. 3A and 3B. However, it should be appreciated that an alternative configuration could be designed without the first and second skip paths 304 and 306 (and therefore using only the main serial path) as shown by FIG. 3B. The CNN 310 does not include any fully connected layer. Additionally, the convolution layers (e.g., 311, 312, 313, 314 and 319) of the example of FIG. 3A includes ReLu and batch normalization (except for the final convolution layers along each path, for which feature maps serve as optimized deformation field components).

The function of the CNN 310 is to learn and generate a non-parametric deformation field, which can be used to map pixels from the first image 300 to pixels of corresponding image components in the second image 302 to identify objects of interest. In other words, the CNN 310 is configured to map pixels from one image to pixels for the same image components in another image, especially pixels that pertain to certain anomalous tissue (i.e., lesions). As such, with respect to the first image 300 and the second image 302, the CNN 310 learns a mapping (or deformation field) between the first and second images 300 and 302.

As noted above, the input to the CNN 310 may be a concatenated pair of mammographic images with dimensions M×N×2. One image is a Craniocaudal image (CC image) (e.g., a two-dimensional Craniocaudal x-ray mammographic image) (i.e., the first image 300) and the other is a Mediolateral Oblique image (MLO image) (e.g., a two-dimensional Mediolateral x-ray image) (i.e., the second image 302). In the top, serial, path of the CNN 310, four convolution layers (conv. 1—311, conv. 2—312, conv. 3—313, conv. 4—314) each operate to generate down sampled feature maps. The first two convolutional layers (i.e., conv. 1—311 and conv. 2—312) are followed by respective pooling layers (e.g., pool 1—315 and pool 2—316) that aggregate the features mapped in the convolutional layers. The use of pooling layers also reduces resolution to lower memory requirements for the system. In an example embodiment, conv. 1-311 may have a 4×4 kernel and an output matrix of 1500×1000 pixels. Pool 1-315 may have a 2×2 stride and an output matrix of about 750×500 pixels. Cony. 2—312 may have a 4×4 kernel and an output of 375×250 pixels while pool 2—316 has a 3×2 stride and output of 187×125 pixels. The third and fourth convolutional layers (conv. 3—313 and conv. 4-314) are followed by two deconvolution layers (deconv. 1—317 and deconv. 2—318), respectively, which up-sample the feature maps back to the same resolution as the resolution of input images (e.g., the first and second images 300 and 302). As such, conv. 3—313 may have a 3×3 kernel and output of 187×125 pixels, deconv. 1—317 may have a 6×6 kernel and an output of 750×125 pixels, conv. 4—314 may have a 3×3 kernel and output of 750×125 pixels, and deconv. 2—318 may have a 6×6 kernel and output of 3000×2000 pixels. A final convolution layer 319 involves two channels (321 and 322), which provide row and column deformation components 323 (e.g., vectors) for the skip paths, and outputs to a deformation field (e.g., deformation field C 334). The final convolutional layer 319 may have a 1×1 kernel and output of 3000×2000 pixels. The vectors or row and column deformation components 323 are applied to the second image 302 (e.g., the MLO image) to move pixels around so that the resulting image (e.g., warped image) look like the first image 300 (e.g., the CC image). This will cause overlap of features and potentially, if a feature corresponds to a lesion, effectively cause the lesion to remain prominent in the warped image. In some cases, the operator can select or click on a feature (e.g., a potential lesion) and alternate through other views (e.g., the CC image or the MLO image) to see the same feature in the other view.

The two skip paths (e.g., the first and second skip paths 304 and 306) each include a deconvolution stage (e.g., stages 342 and 340, respectively) and a convolution stage (e.g., stages 346 and 344, respectively). The skip paths also generate additional deformation fields (e.g., deformation field A 330 and deformation field B 332) based on information at earlier stages in the network. The resulting deformations from each of the paths (e.g., deformation field A 330, deformation field B 332, and deformation field C 334) may be up-sampled to the same resolution as the input images (e.g., the first and second images 300 and 302—3000×2000 pixels in this example), averaged, and used to warp desired regions of one of the input channels to corresponding regions of the other input channel by loss function 350.

The deformation field involves two, two-dimensional arrays, one containing vertical (row-wise) deformation components and one containing horizontal (column-wise) deformation components. Together, these constitute a two-dimensional deformation vector. (The general network architecture could also be extended to generate a three-dimensional deformation field.) Convolution layers 319, 344 and 346 in FIG. 3A, and 319 in FIG. 3B generate the two arrays (also known as feature maps). Modules associated with generating deformation fields (e.g., 334, 332, and 330), take the deformation components and use them to shift each pixel in the MLO input image to the location constituted by the corresponding deformation vector. The deformation equation is essentially, as shown below, where x and y are row an column coordinates for a specific pixel in the input MLO image. The x coordinate is translated by a vector, u, that is formed from values that are at the same array position in the vertical and horizontal deformation component arrays. The y coordinate is translated in similar fashion using vector, v.

$$Im_{def}(x,y) = Im(x+u(x,y), y+v(x,y))$$

(Note: u and v are rounded to serve as indices)

As noted earlier, during training, the network layer parameters, such as convolutional and pooling kernel sizes are set dynamically based on the size of the input images.

Optimization may be performed using the loss function 350 involving a similarity metric and one or more regularization techniques. One example of the loss function 350 is shown below.

Example Loss Function (for one path of the network).
Loss=$\Sigma_{i=1}^{L}|Y_i-T_i|+\lambda\Sigma_{i=1}^{L}\|\nabla d(i)\|_1$, where, Y is the resulting warped image by the network, T, is the target image, d, is the deformation field, and L is the number of pixels in the image. (The loss from each network path is weighted and summed)

$$Ln = S(I_1(x), I_2(D_n(x))) + \lambda R(D_{nx}), \text{ where } n=A, B, \text{ or } C.$$

The output of the CNN 310 may include a warped image 360 based on the application of the deformation fields to the respective input image (e.g., second image 302) which needs to be registered to the target image (e.g., first image 300), and a deformation field 365 showing vector movement of pixels between the first and second images 300 and 302. Object identification 370 may then be performed to indicate an object that is common to both the input image and the target image by using the deformation field to provide a functionality such as allowing a user to click on the original input MLO image and having the system—using the deformation field for a mapping—to show the corresponding tissue on the CC image. The provision of the deformation field 365 may also support implementation of other functions for generating visualizations related to determining correspondences between features in the first and second images 300 and 302 (e.g., from original positions in one image to final positions in the other). Further, the deformation field output may support other machine learning or image processing systems by providing a means (i.e., the deformation-based mapping) for relating pixel or object detections in one image to the other.

Figure 4:
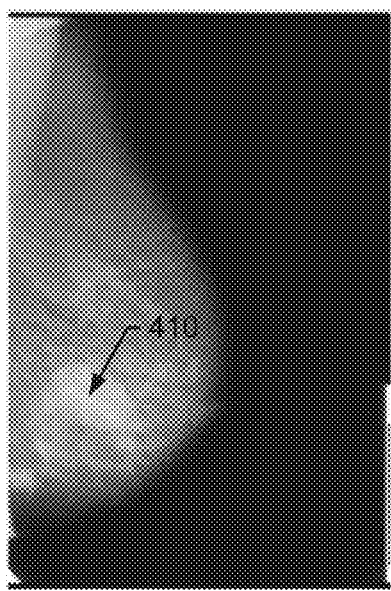
FIG. 4 illustrates an MLO image with a potential lesion in accordance with an example embodiment.
Figure 5:
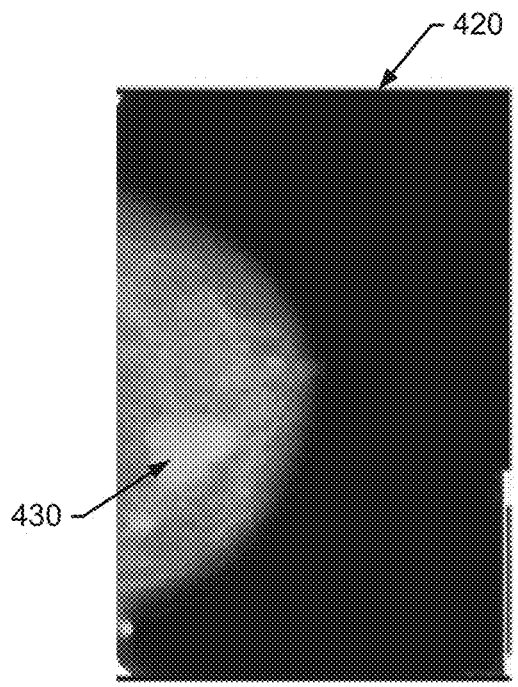
FIG. 5 illustrates a CC image with a potential lesion in accordance with an example embodiment.
Figure 6:
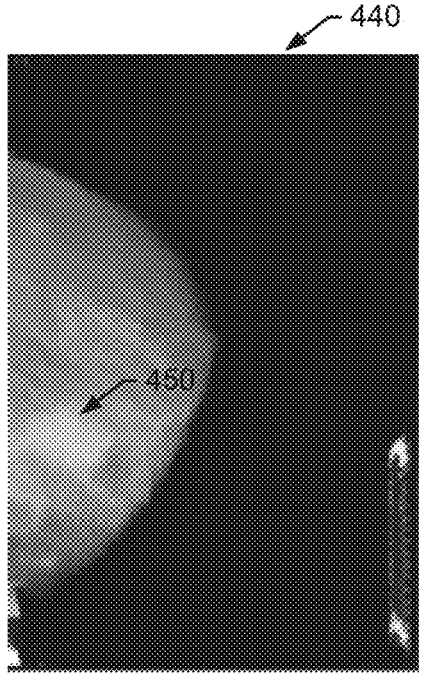
FIG. 6 illustrates a warped image created by pixel level registration of the images of FIGS. 4 and 5 in accordance with an example embodiment.
Figure 7:
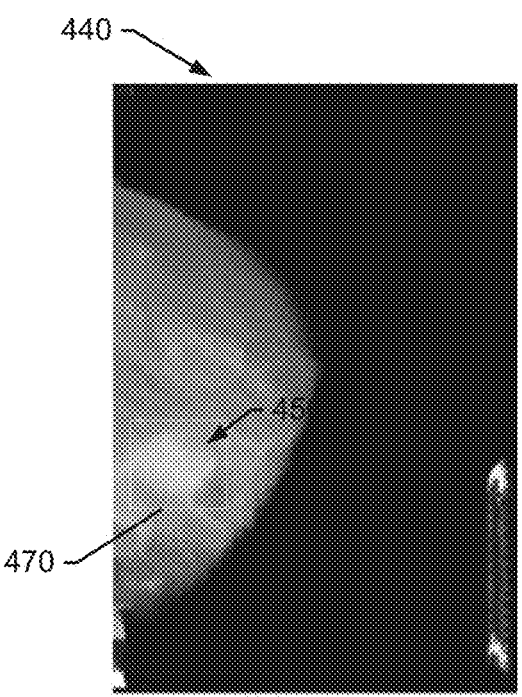
FIG. 7 illustrates the warped image along with an object identification indicating a potential lesion in accordance with an example embodiment.

FIGS. 4-7 show an example of images (e.g., using de-identified data) and results that may be involved in the operation of the CNN 310 of FIG. 3A. In this regard, FIG. 4 shows an MLO image 400 with a candidate object 410 visible therein. FIG. 5 shows a CC image 420 with a candidate object 430 visible therein. Either of the MLO image 400 or the CC image 420 could act as the input image or the target image. In either case, one of the images will be warped to the other. In the example of FIG. 6, the MLO image 400 has been warped to the CC image 420 to generate warped image 440. Although not required, masks or other image processing techniques could be used to address background or burned-in annotations. However, in this case, candidate combined object 450, which is visible in the warped image 440, appears to correlate to both the candidate object 410 and candidate object 430 without any need for additional processing. As such, the object identification 470 may be added to the warped image 440 to highlight the candidate combined object 450 to a practitioner (e.g., a radiologist) for evaluation.

Figures 8, 9, 10, 11:
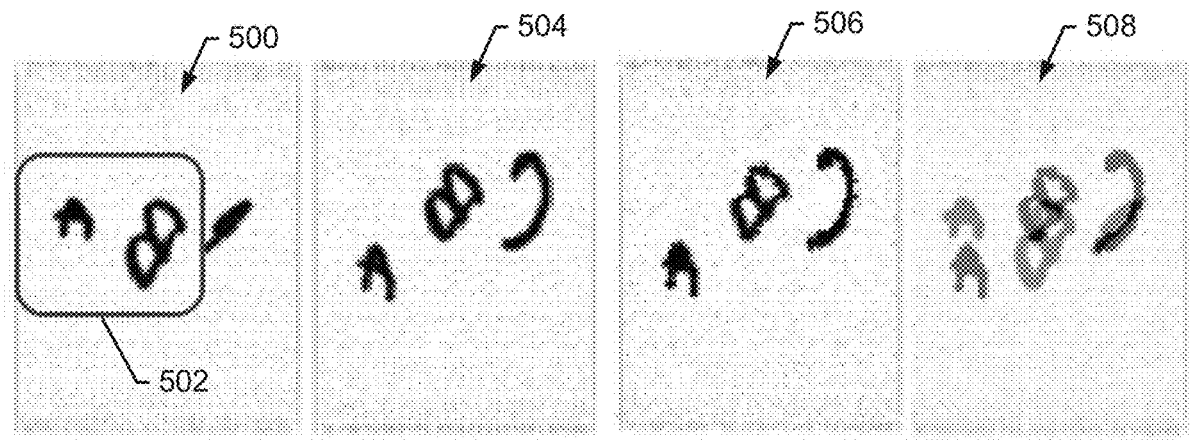
FIG. 8 illustrates sample objects in a volume in accordance with an example embodiment.
FIG. 9 illustrates the sample objects of FIG. 8 moved slightly to facilitate demonstration of the operation of an example embodiment of pixel level registration.
FIG. 10 shows a post registration view corresponding to FIGS. 8 and 9 in accordance with an example embodiment.
FIG. 11 illustrates a before and after view with respect to registration in accordance with an example embodiment.

Performance of the architecture of FIG. 3A has also been tested on surrogate three dimensional (3-D) Mixed National Institute of Standards and Technology (MNIST) letters and is demonstrated in relation to FIGS. 8-12. In this regard, FIG. 8 illustrates a first image 500 (e.g., a 2-D image) of three letters, two of which are located in a highlighted region 502, randomly placed in a 3-D space (e.g., a cylinder). The letter orientations or positions may then be slightly altered to simulate some level of non-rigidity of the objects and then the 3-D space is rotated about the x-axis about 45 degrees (e.g., 40-50 degrees). The second image 504 of FIG. 9 is then captured. If the first image 500 is considered to be an input image (i.e., the image to register), and the second image 504 is considered the target image, deformation fields generated by the CNN 310 of FIG. 3A may serve to translate pixels from the input image to the corresponding locations in the target image (thereby warping the input image to the translated image). A registration result 506 is shown in FIG. 10. Meanwhile, FIG. 11 shows a before and after view 508 for before and after registration.

Figure 12:
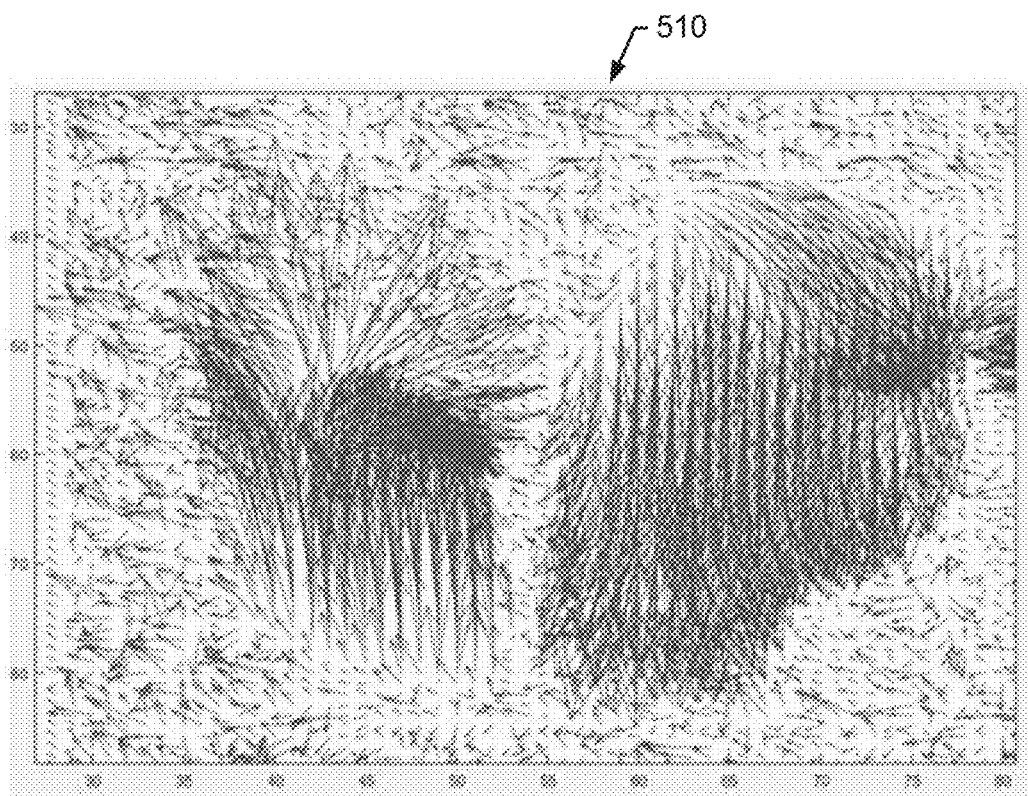
FIG. 12 is a quiver plot showing the deformation field in the highlighted region of FIG. 8 in accordance with an example embodiment.

The projections associated with FIGS. 8-11 can serve as two-channel inputs to the CNN 310 of FIG. 3A. Each of the images of FIGS. 8-11 are images of 1024×1024 pixels to demonstrate performance in a high-resolution environment. However, testing with lower resolution performance (e.g., 128×128 pixels) is also possible. In an example embodiment, 9000 random projection pairs were generated (therefore 18,000 total images) and 90% of the projection pairs were used for training, while 10% were used for testing. For the simplistic modeling associated with FIGS. 8-11, the test results clearly demonstrate the high degree to which example embodiments are able to warp an input image (or moving image) to a target image (or fixed image). FIG. 12 shows a quiver plot 510 of deformation field vectors for the highlighted region 502 of FIG. 8. Thus, FIG. 12 shows pixel level registration of the letter projections in the highlighted region 502 to illustrate how the pixels for the letters A and B moved from FIG. 8 to FIG. 9. With additional training data, the possibility of refining network performance even further may also exist. However, the examples of FIGS. 4-12 clearly demonstrate the ability of the image registration module 60 to employ the first sub-method (i.e., pixel level registration with CNN deformation field learning) to effectively perform registration between CC and MLO image data, and to identify the same objects appearing in both.

Figure 13:
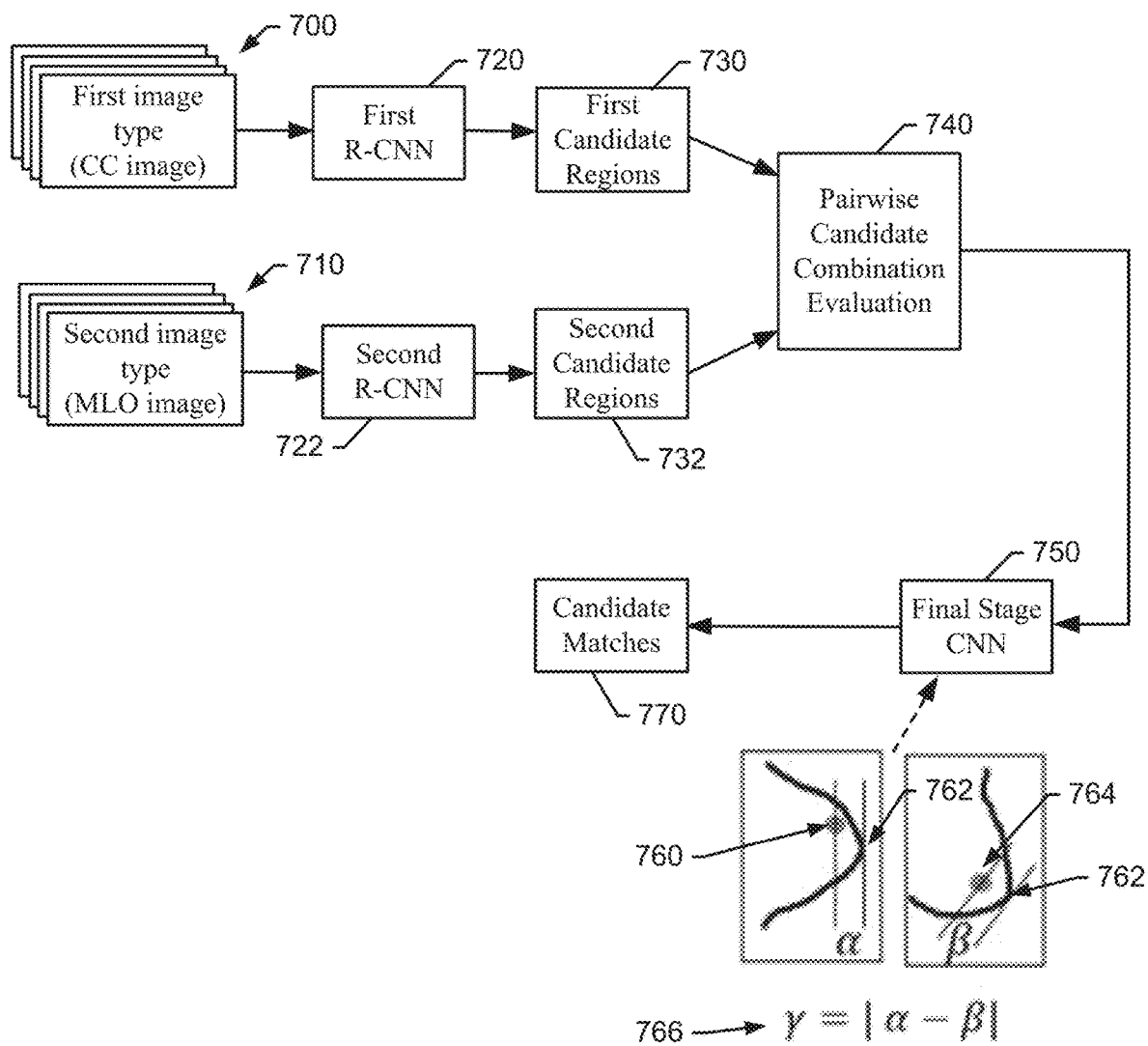
FIG. 13 illustrates an architecture for performing the method of FIG. 2 using object level registration in accordance with an example embodiment.

As noted above, the image registration module 60 may also employ the second sub-method (i.e., object level registration). FIG. 13 illustrates an architecture that can be used to support object level registration in accordance with an example embodiment. The architecture of FIG. 13 employs a CNN architecture known as region-based CNN (R-CNN) The R-CNN architecture may be employed based on the descriptions by R. Girshick, J. Donahue, T. Darrell, and J. Malik in "Rich Feature Hierarchies for Accurate Object Detection and Semantic Segmentation," from *CVPR '14 Proceedings of the* 2014 *IEEE Conference on Computer Vision and Pattern Recognition* at pages 580-587, 2014, the contents of which are hereby incorporated herein by reference. In this regard, FIG. 13 illustrates a two-stage, dual R-CNN based architecture in which the first stage includes two R-CNNs that process respective image sets to find candidate objects isolated to the respective images sets themselves. Then the second stage includes another CNN that is configured to process output pairs from the first stage.

As shown in FIG. 13, a first set of images 700 may include a plurality of images of a first image type (e.g., CC images), and a second set of images 710 may include a plurality of images of a second image type (e.g., MLO images). The first set of images 700 may be fed into a first R-CNN 720 and the second set of images 710 may be separately fed into a second R-CNN 722. The first and second R-CNNs 720 and 722 are disconnected, and do not have any connection therebetween. Additionally, whereas a conventional CNN processes an entire image, the first and second R-CNNs 720 and 722 may be configured to first identify one or more smaller candidate regions within an image and process only those smaller candidate regions. The processing of smaller regions means that less memory is required for the processing. The candidate regions are not fixed regions, but may be regions selected based on a region proposal function associated with the CNN. Accordingly, the first and second R-CNNs 720 and 722 may require less memory for processing, and can therefore be expected to handle larger images. The ability to handle larger images is important for medical image processing since it is important to maintain the original pixel resolution of source images to preserve subtle differences in texture.

Figure 20:
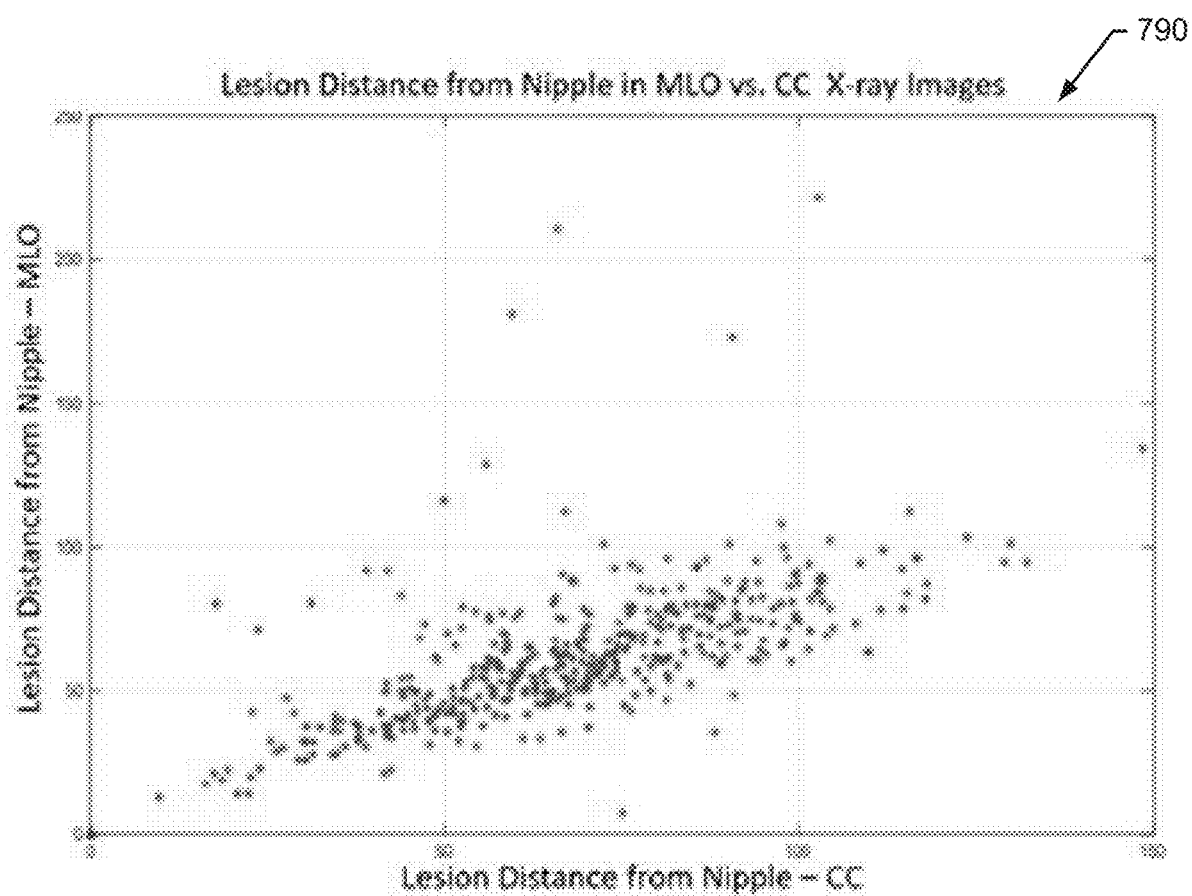
FIG. 20 illustrates a plot of lesion distance from nipple for MLO and CC images in accordance with an example embodiment.

When the first set of images 700 is received by the first R-CNN 720, the first R-CNN 720 operates to generate a series of first candidate regions 730 based on analysis of the first set of images 700. The first candidate regions 730 may each identify regions that include potential lesions based on a scoring value generated by the first R-CNN 720. Similarly, the second R-CNN 722 operates to generate a series of second candidate regions 732 based on analysis of the second set of images 710. The second candidate regions 732 are also identified regions that may include lesions based on a scoring value generated by the second R-CNN 722. A pairwise candidate combination evaluation 740 is then performed, potentially over a number of different combinations of pairs. The scoring values may be used filter out certain combinations of pairs, and remaining pairs (i.e., those not filtered out, and therefore having scoring values above a threshold value) may be merged into a two-image-layer product. However, a third layer or band may be generated prior to final processing by final stage CNN 750. The third band may be generated based on an absolute difference between relative distances-from-nipple for each potential detection. In this regard, $\alpha$ shows a distance from a potential detection 760 and a nipple 762 for a CC image, and $\beta$ shows a distance from a potential detection 764 and the nipple 762. Equation 766 shows how $\gamma$ may then be calculated based on the absolute difference between $\alpha$ and $\beta$. $\gamma$ may be provided as a layer in the second stage CNN. The CNN may use the $\gamma$ and, based on a statistical correlation between lesions in CC and MLO images, $\gamma$ may facilitate finding image patches that go together via the CNN. Patches that are significantly different distances from the nipple do not likely belong together since a lesion should have the same distance from the nipple in both CC and MLO views. FIG. 20 shows a graph 790 of lesion distance from nipple in MLO images to the lesion distance from nipple in CC images. In this regard, FIG. 20 shows a linear correlation in the relative lesion-to-nipple distance for the same lesions in both views.

Accordingly, a three-image-layer input is provided to the final stage CNN 750, and the final stage CNN 750 operates to classify each set of pair candidates (between CC and MLO images) as either matching or not-matching based on a lower $\gamma$ indicating a greater likelihood of a match. Candidate matches 770 may therefore be generated from the candidate pairs that are classified as matching. The candidate matches 770 may therefore be understood to illustrate detections of the same object (e.g., a potential lesion) in both of the different types of images (CC and MLO images).

Figure 14:
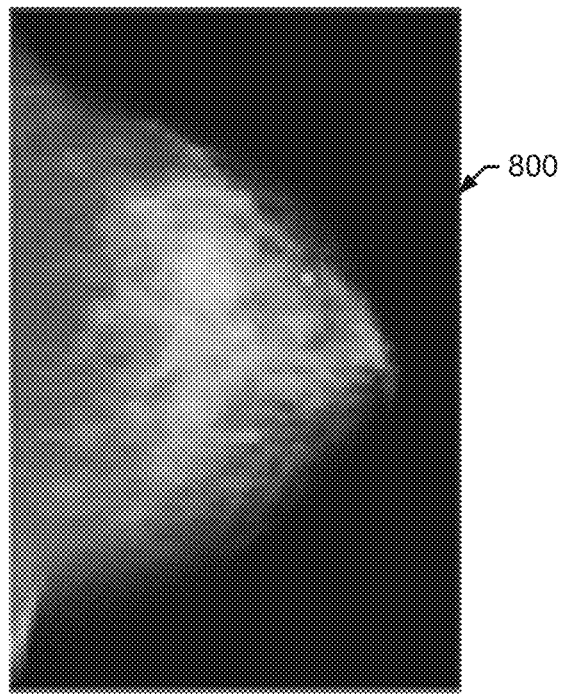
FIG. 14 illustrates a CC image with a potential lesion in accordance with an example embodiment.
Figure 15:
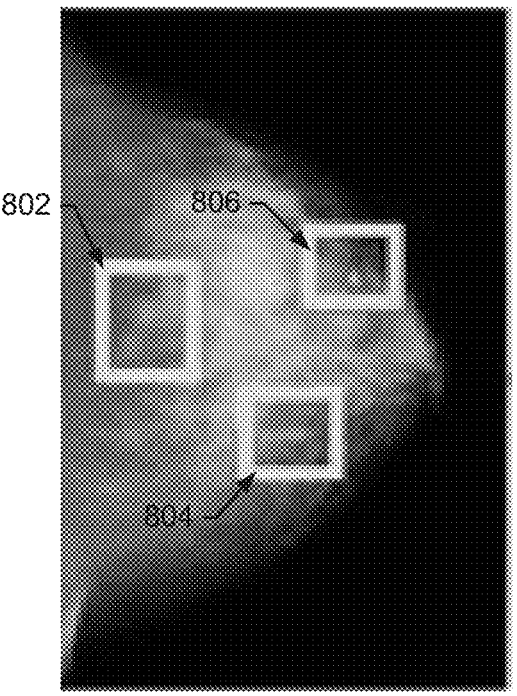
FIG. 15 illustrates the CC image with candidate regions identified in accordance with an example embodiment.
Figure 16:
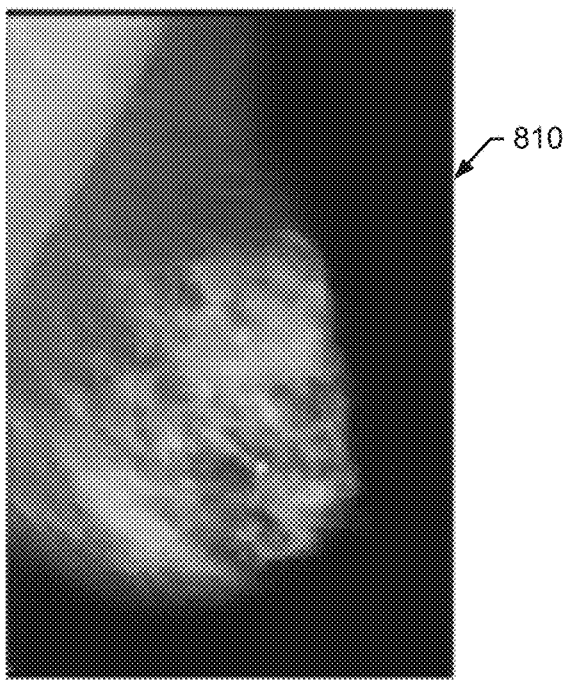
FIG. 16 illustrates an MLO image with a potential lesion in accordance with an example embodiment.
Figure 17:
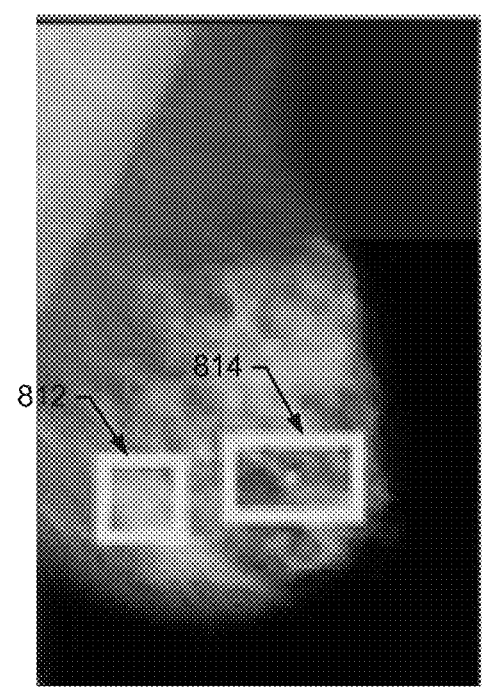
FIG. 17 illustrates the MLO image with candidate regions identified in accordance with an example embodiment.

An example is shown in FIGS. 14-19 to demonstrate the operation of the sub-method shown in FIG. 13. In this regard, FIG. 14 illustrates a CC image 800 that may be one of the first set of images 700 of FIG. 13. FIG. 15 illustrates a first candidate region 802, a second candidate region 804 and a third candidate region 806 that may be generated as the first candidate regions 730 of FIG. 13 due to operation of the first R-CNN 720. FIG. 16 illustrates an MLO image 810 that may be one of the second set of images 710 of FIG. 13. FIG. 17 illustrates a fourth candidate region 812, and a fifth candidate region 814 that may be generated as the second candidate regions 732 of FIG. 13 due to operation of the second R-CNN 722.

Figure 18:
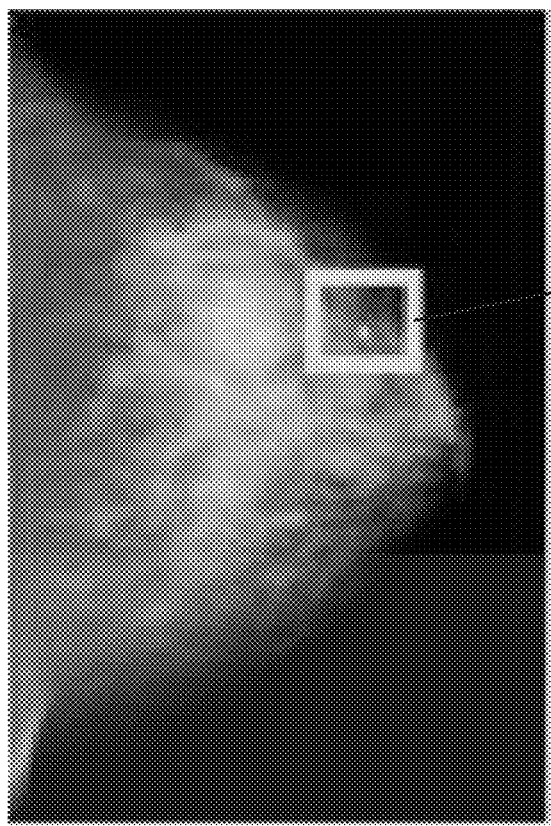
FIG. 18 illustrates the CC image with a candidate match highlighted in accordance with an example embodiment.
Figure 19:
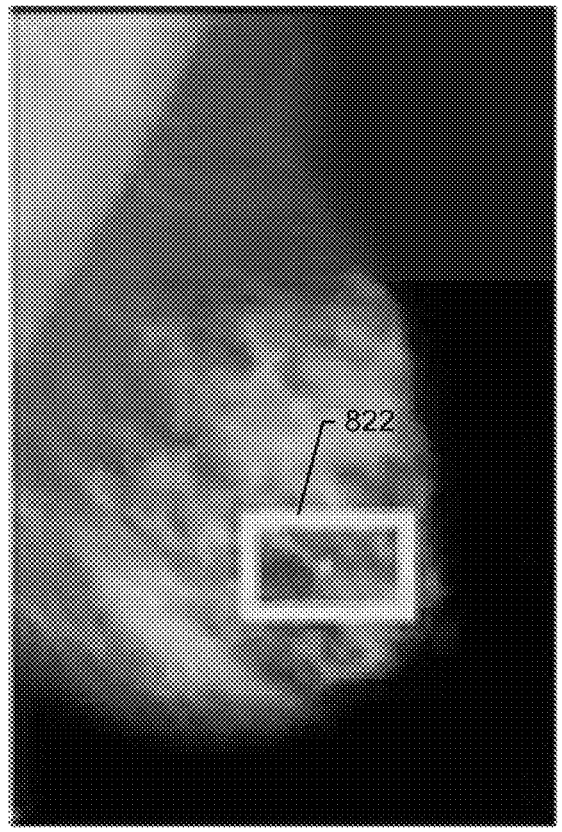
FIG. 19 illustrates the MLO image with a candidate match highlighted in accordance with an example embodiment.

The pairwise candidate combination evaluation 740 may then be performed along with processing by the final stage CNN 750 to produce candidate matches 770 shown in FIGS. 18 and 19. In this regard, FIG. 18 shows the CC image 800, with candidate match 820 highlighted thereon. Similarly, FIG. 19 shows the MLO image 810 with candidate match 822 highlighted thereon. The candidate matches 820 and 822 may enable a practitioner (e.g., radiologist) to quickly and easily evaluate the CC and MLO image data.

Figure 21:
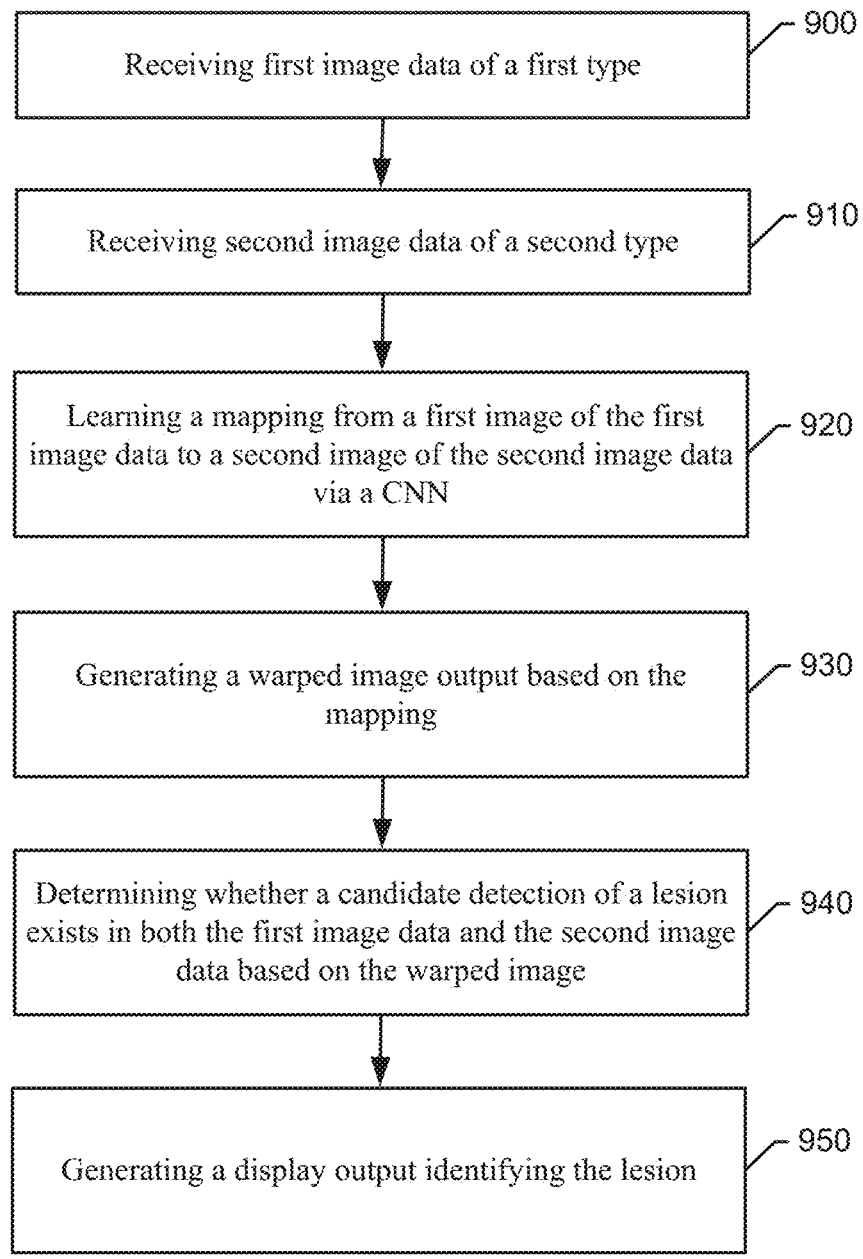
FIG. 21 illustrates a functional block diagram of a method for identifying potential lesions in mammographic images via pixel level registration according to an example embodiment.

Based on the descriptions above, it can be appreciated that the method of FIG. 2 defines a general methodology for detecting potential lesions in two different types of images (e.g., CC and MLO images). The general methodology may include either (or both) of two individual sub-methods that have been separately described above. FIG. 21 illustrates a block diagram of one of those sub-methods (i.e., using pixel level registration) and FIG. 22 illustrates a block diagram of the other of those sub-methods (i.e., using object level registration).

Referring now to FIG. 21, a method of identifying potential lesions in mammographic images via pixel level registration, which can be executed by an image processing device is provided. The method may include receiving first image data of a first type at operation 900, and receiving second image data of a second type at operation 910. The method may further include employing a CNN to learn a mapping from a first image of the first image data to a second image of the second image data at operation 920, and generating a warped image output based on the mapping at operation 930. The method may also include determining whether a candidate detection of a lesion exists in both the first image data and the second image data based on the warped image at operation 940, and generating a display output identifying the lesion (e.g., an object identification illustrating the candidate detection) at operation 950.

In some embodiments, the features or operations described above may be augmented or modified, or additional features or operations may be added. These augmentations, modifications and additions may be optional and may be provided in any combination. Thus, although some example modifications, augmentations and additions are listed below, it should be appreciated that any of the modifications, augmentations and additions could be implemented individually or in combination with one or more, or even all of the other modifications, augmentations and additions that are listed. As such, for example, the method may further include application of a skip architecture within the CNN. The skip architecture may include one or more skip paths, and each of the one or more skip paths may generate a corresponding deformation field. In some cases, the first image data is two-dimensional CC mammographic image data and the second image data is two-dimensional MLO mammographic image data. In an example embodiment, determining whether the candidate detection exists in both the first image data and the second image data may include analyzing the warped image output for correlated features associated with the candidate detection, and generating the object identification may include generating the object identification on the warped image. In some cases, the CNN may be a fully convolutional network. Alternatively or additionally, the CNN may be configured so that it does not include any fully connected layer. Also, the first image data and the second image data may be input to the CNN in separate channels such that an output of the CNN comprises two channels defining row and column deformation components.

Figure 22:
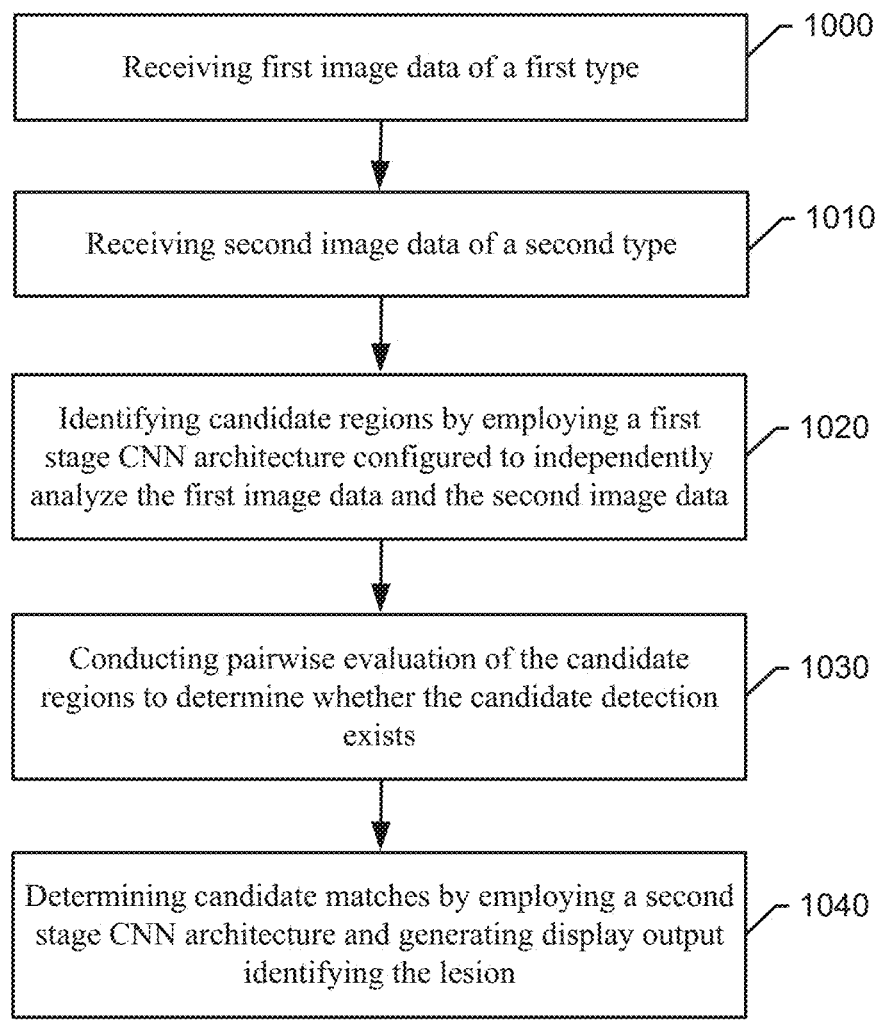
FIG. 22 illustrates a functional block diagram of a method for identifying potential lesions in mammographic images via object level registration according to an example embodiment.

Referring now to FIG. 22, a method of identifying potential lesions in mammographic images via object level registration is provided. The method may be executed by an image processing device and may include receiving first image data of a first type at operation 1000, receiving second image data of a second type at operation 1010, and identifying candidate regions by employing a first stage CNN architecture configured to independently analyze the first image data and the second image data to identify the candidate regions at operation 1020. The method may further include conducting pairwise evaluation of the candidate regions to determine whether the candidate detection exists at operation 1030, and determining candidate matches by employing a second stage CNN architecture and generating display output identifying the lesion at operation 1040.

In some embodiments, the features or operations described above may be augmented or modified, or additional features or operations may be added. These augmentations, modifications and additions may be optional and may be provided in any combination. Thus, although some example modifications, augmentations and additions are listed below, it should be appreciated that any of the modifications, augmentations and additions could be implemented individually or in combination with one or more, or even all of the other modifications, augmentations and additions that are listed. As such, for example, the first image data may be two-dimensional CC mammographic image data and the second image data is two-dimensional MLO mammographic image data. In an example embodiment, employing the first stage CNN architecture may include providing a plurality of first images associated with the first image data to a first R-CNN trained to identify first candidate regions, and providing a plurality of second images associated with the second image data to a second R-CNN trained to identify second candidate regions. The first and second candidate regions may include the candidate regions on which the pairwise evaluation is conducted. In an example embodiment, employing the second stage CNN architecture may include providing the second stage CNN architecture with data associated with the first candidate regions and the second candidate regions, and distance from nipple information for each instance of the candidate detection in the data associated with the first candidate regions and the second candidate regions. In some cases, generating the object identification may include generating the object identification on both the first images and the second images.

From a technical perspective, the image registration module 60 described above may be used to support some or all of the operations described above. As such, the platform described in FIG. 1 may be used to facilitate the implementation of several computer program and/or network communication based interactions. As an example, FIGS. 2, 21 and 22 are each examples of a flowchart of a method and program product according to an example embodiment of the invention. It will be understood that each block of the flowchart, and combinations of blocks in the flowchart, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory device of a user terminal and executed by a processor in the user terminal. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block(s). These computer program instructions may also be stored in a computer-readable memory that may direct a computer or other programmable apparatus to function in a particular manner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In an example embodiment, an apparatus for performing the method of FIG. 2, 21 or 22 above may comprise a processor (e.g., the processor 102) or processing circuitry configured to perform some or each of the operations (200-220, 900-950 and 1000-1040) described above. The processor may, for example, be configured to perform the operations (200-220, 900-950 and 1000-1040) by performing hardware implemented logical functions, executing stored instructions, or executing algorithms for performing each of the operations. In some embodiments, the processor or processing circuitry may be further configured to perform the additional operations or optional modifications to operations 200-220, 900-950 and 1000-1040 that are discussed above.

Example embodiments provide a fully convolutional (versus fully connected) CNN that is non-rigid deformation-field based. In this regard, since breast tissue is non-rigid and heterogeneous in nature, such a characteristic of the network is important to successful registration within this context. The environment or context in which example embodiments operate is particularly challenging since the breast tissue is compressed and repositioned in the different views used, and since the viewing angles employed between the views used are also different. The CNN employed by example embodiments can therefore register images to find correspondences between images (e.g., salient features, which may be bright features in the CC or MLO images) that are different in these important ways. Example embodiments may also be capable of operating at the pixel level within this challenging context. Example embodiments are also distinct from other architectures (e.g., Siamese architectures) since these architectures share network weights between paths. Meanwhile, example embodiments do not share weights between paths so that each path is unique and has its own weights, and can learn independently of the other path.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A method of identifying potential lesions in mammographic images, the method comprising:
   receiving, by an image processing device, first image data;
   receiving, by the image processing device, second image data, one of the first image data or the second image data being two-dimensional Craniocaudal (CC) mammographic image data or two-dimensional Mediolateral Oblique (MLO) mammographic image data;
   registering, by the image processing device, the first image data and the second image data by employing an image registration convolutional neural network (CNN) using pixel level registration; wherein registering the first image data with the second image data comprises:
   inputting the first image data and the second image data into the image registration CNN;
   generating, via convolutions performed by the image registration CNN on the first image data and the second image data, a deformation field of deformation vectors that map pixels of the first image data to pixels of the second image data; the deformation field comprising, to define the deformation vectors,
      a vertical deformation data array that defines row-wise relationships between the pixels of the first image data and the pixels of the second image data and
      a horizontal deformation data array that defines column-wise relationships between the pixels of the first image data and the pixels of the second image data;
   determining, by the image processing device, whether a candidate detection of a lesion exists in both the first image data and the second image data based on the first image data and the second image data and a mapping of the first image data to the second image data provided by deformation field output from the image registration CNN; and
   generating, by the image processing device, display output identifying the lesion.

2. The method of claim 1, wherein the first image data is two-dimensional Craniocaudal (CC) mammographic image data and the second image data is two-dimensional Mediolateral Oblique (MLO) mammographic image data.

3. The method of claim 2, wherein generating the deformation field comprises:
   learning a mapping from a first image of the first image data to a second image of the second image data via the CNN; and
   generating a warped image output based on the mapping.

4. The method of claim 3, wherein determining whether the candidate detection exists in both the first image data and the second image data comprises analyzing the warped image output for correlated features associated with the candidate detection, and
   wherein generating the display output comprises generating an object identification on the warped image.

5. The method of claim 3, wherein the CNN is a fully convolutional network,
   wherein the CNN does not include any fully connected layer, and wherein the first image data and the second image data are input to the CNN in separate channels such that an output of the CNN comprises two channels defining the vertical deformation data array and the horizontal deformation data array.

6. The method of claim 3, wherein the CNN comprises a skip architecture including one or more skip paths, and
wherein each of the one or more skip paths is implemented to generate the deformation field.

7. The method of claim 2, further comprising performing object level registration, wherein performing object level registration comprises:
employing a first stage CNN architecture configured to independently analyze the first image data and the second image data to identify candidate regions;
conducting pairwise evaluation of the candidate regions to determine whether the candidate detection exists; and
employing a second stage CNN architecture configured to determine candidate matches and generate object identification based on the pairwise evaluation.

8. The method of claim 7, wherein employing the first stage CNN architecture comprises:
providing a plurality of first images associated with the first image data to a first region-based CNN (R-CNN) trained to identify first candidate regions; and
providing a plurality of second images associated with the second image data to a second R-CNN trained to identify second candidate regions,
wherein the first and second candidate regions comprise the candidate regions on which the pairwise evaluation is conducted.

9. The method of claim 8, wherein employing the second stage CNN architecture comprises providing the second stage CNN with data associated with the first candidate regions and the second candidate regions, and distance from nipple information for each instance of the candidate detection in the data associated with the first candidate regions and the second candidate regions.

10. The method of claim 9, wherein generating the display output comprises generating an object identification on both the first images and the second images.

11. The method of claim 2, further comprising utilizing both the pixel level registration to generate a first object identification and an object level registration to generate a second object identification, and comparing the first and second object identifications.

12. A method of identifying potential lesions in mammographic images, the method comprising:
receiving, by an image processing device, first image data of a first type;
receiving, by the image processing device, second image data of a second type;
learning, by the image processing device, a mapping from a first image of the first image data to a second image of the second image data by employing an image registration convolutional neural network (CNN) to perform pixel level registration between the first image data and the second image data, wherein registering the first image data with the second image data comprises:
inputting the first image data and the second image data into the image registration CNN;
generating, via convolutions performed by the image registration CNN on the first image data and the second image data, a deformation field of deformation vectors that map pixels of the first image data to pixels of the second image data; the deformation field comprising, to define the deformation vectors,
a vertical deformation data array that defines row-wise relationships between the pixels of the first image data and the pixels of the second image data and
a horizontal deformation data array that defines column-wise relationships between the pixels of the first image data and the pixels of the second image data;
generating, by the image processing device as an output of the image registration CNN based on the deformation field, a warped image output of the first image data mapped to the second image data using the deformation field;
determining, by the image processing device, whether a candidate detection of a lesion exists in both the first image data and the second image data based on the warped image; and
generating, by the image processing device, display output identifying the lesion.

13. The method of claim 12, wherein the first image data is two-dimensional Craniocaudal (CC) mammographic image data and the second image data is two-dimensional Mediolateral Oblique (MLO) mammographic image data.

14. The method of claim 13, wherein determining whether the candidate detection exists in both the first image data and the second image data comprises analyzing the warped image output for correlated features associated with the candidate detection, and
wherein generating the display output comprises generating an object identification on the warped image.

15. The method of claim 13, wherein the CNN is a fully convolutional network,
wherein the CNN does not include any fully connected layer, and
wherein the first image data and the second image data are input to the CNN in separate channels such that an output of the CNN comprises two channels defining the vertical deformation data array and the horizontal deformation data array.

16. The method of claim 13, wherein the CNN comprises a skip architecture including one or more skip paths, and
wherein each of the one or more skip paths is implemented to generate the deformation field.

17. A method of identifying potential lesions in mammographic images, the method comprising:
receiving, by an image processing device, first image data of a first type;
receiving, by the image processing device, second image data of a second type;
identifying, by the image processing device, candidate regions via a first stage convolutional neural network (CNN) architecture configured to independently analyze the first image data using a first region-based convolutional neural network (R-CNN) to identify first candidate regions and independently analyze the second image data using a second R-CNN to identify second candidate regions, and perform object level registration of the first candidate regions with the second candidate regions candidate regions;
conducting, by the image processing device, pairwise evaluation of the first candidate regions with the second candidate regions to determine sets of pair candidates; and
determining, by the image processing device, candidate matches via a second stage CNN architecture comprising a second stage CNN that is applied to the sets of pair candidates, and generating a display output illustrating the candidate matches, wherein the second stage CNN is independent from the first R-CNN and the second R-CNN.

18. The method of claim 17, wherein the first image data is two-dimensional Craniocaudal (CC) mammographic image data and the second image data is two-dimensional Mediolateral Oblique (MLO) mammographic image data.

19. The method of claim 18, wherein employing the second stage CNN architecture comprises providing the second stage CNN architecture with data associated with the first candidate regions and the second candidate regions, and distance from nipple information for each instance of the sets of pair candidates in the data associated with the first candidate regions and the second candidate regions.

20. The method of claim 19, wherein generating the display output comprises generating an object identification on both the first images and the second images.

* * * * *